United States Patent [19]
Middeldorp

[11] Patent Number: 5,843,405
[45] Date of Patent: Dec. 1, 1998

[54] EPSTEIN-BARR VIRUS PEPTIDES AND ANTIBODIES AGAINST THESE PEPTIDES

[75] Inventor: Jaap Michiel Middeldorp, Oss, Netherlands

[73] Assignee: Akzo Nobel N.V., Arnhem, Netherlands

[21] Appl. No.: 660,789

[22] Filed: Jun. 6, 1996

[30] Foreign Application Priority Data

Jun. 6, 1995 [EP] European Pat. Off. .............. 95201486

[51] Int. Cl.$^6$ ........................... A61K 49/00; A61K 38/00
[52] U.S. Cl. .......................... 424/9.34; 530/300; 530/811
[58] Field of Search .................................. 530/300, 811; 424/9.34

[56] References Cited

U.S. PATENT DOCUMENTS

| | | | |
|---|---|---|---|
| 4,761,470 | 8/1988 | Emini | 530/326 |
| 4,879,213 | 11/1989 | Fox et al. | 435/5 |
| 5,087,557 | 2/1992 | McClure | 435/5 |
| 5,256,768 | 10/1993 | Milman . | |

FOREIGN PATENT DOCUMENTS

| | | |
|---|---|---|
| A 0 173 254 | 3/1986 | European Pat. Off. . |
| A 0 280 813 | 9/1988 | European Pat. Off. . |

OTHER PUBLICATIONS

R.I. Fox et al., *Journal of Clinical Laboratory Analysis*, 1:1:140–145, 1987.

*Primary Examiner*—Ponnathapura Achutamurthy
*Assistant Examiner*—Hankyel T. Park
*Attorney, Agent, or Firm*—Mary E. Gormley; Sharon N. Klesner

[57] ABSTRACT

The invention relates to peptides or fragments thereof which are immunochemically reactive with Epstein-Barr Virus (EBV) antibodies. New antibodies directed to said peptides or fragments thereof are also part of the invention.

The invention also relates to a method for the detection of EBV or antibodies directed against EBV in a test fluid and also to an immunochemical reagent comprising a peptide, a fragment or a polypeptide according to the invention and a test kit to be used when applying the said detection methods.

Detection of EBV in a test fluid or tissue specimen using antibodies, monoclonal and polyclonal, directed to the said peptide, which have the characteristics of detecting both native and denatured EBV-EA protein is also part of said invention.

8 Claims, 16 Drawing Sheets

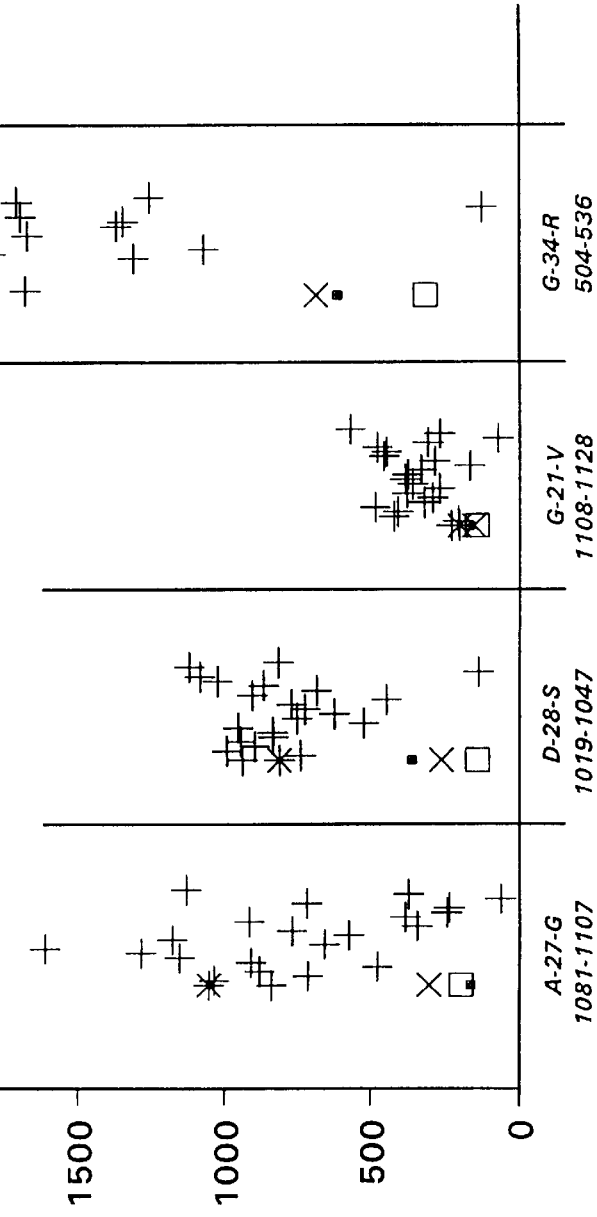

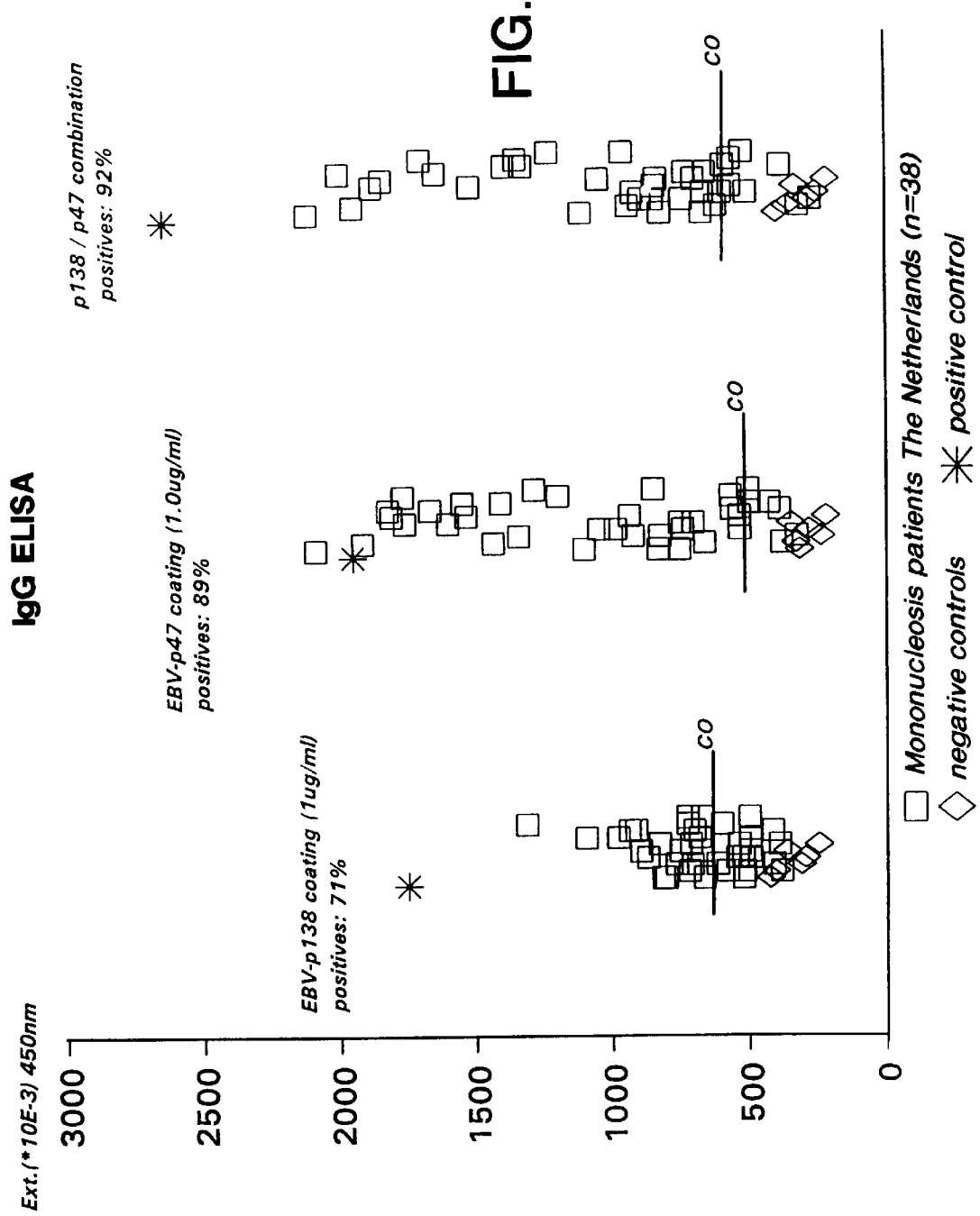

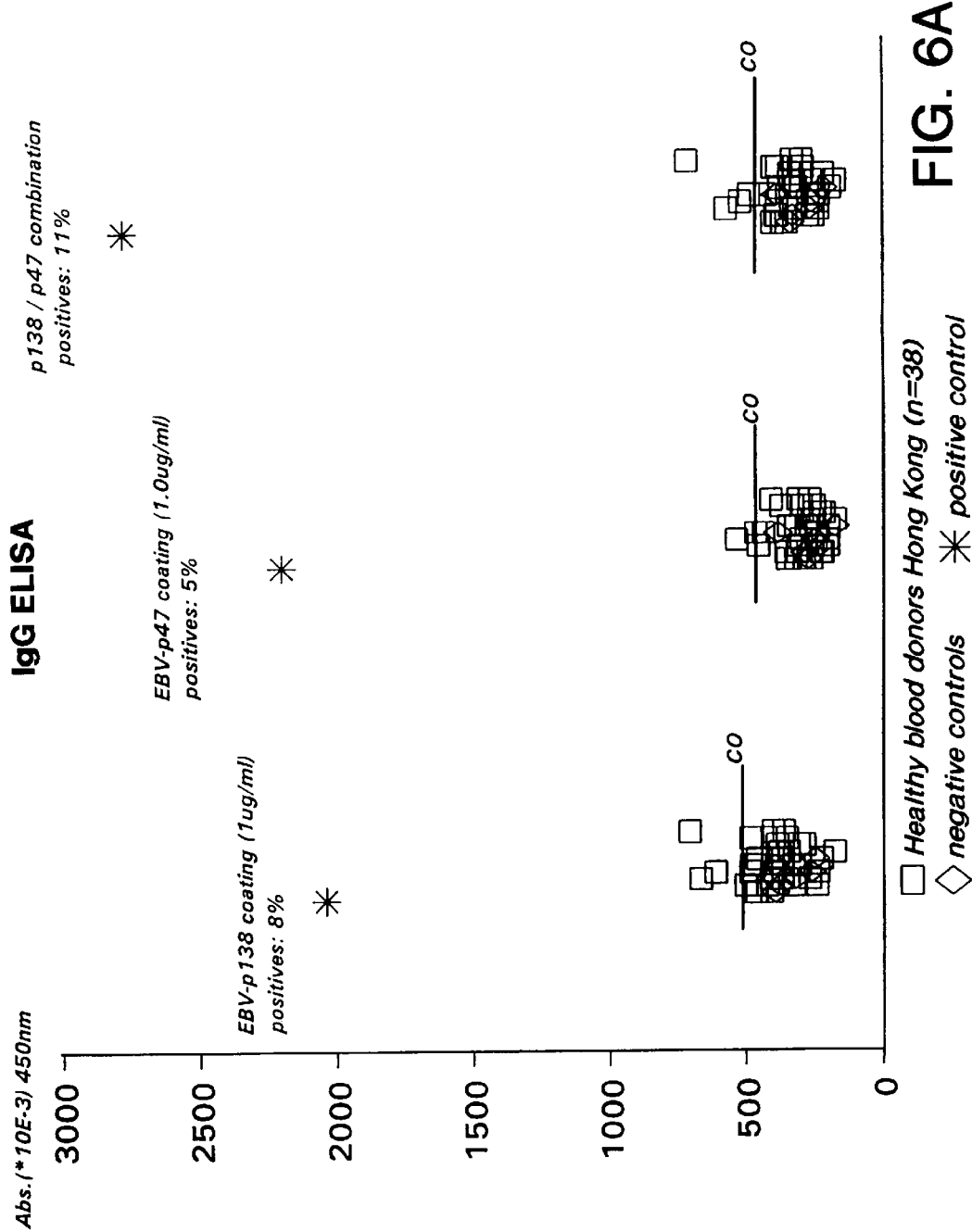

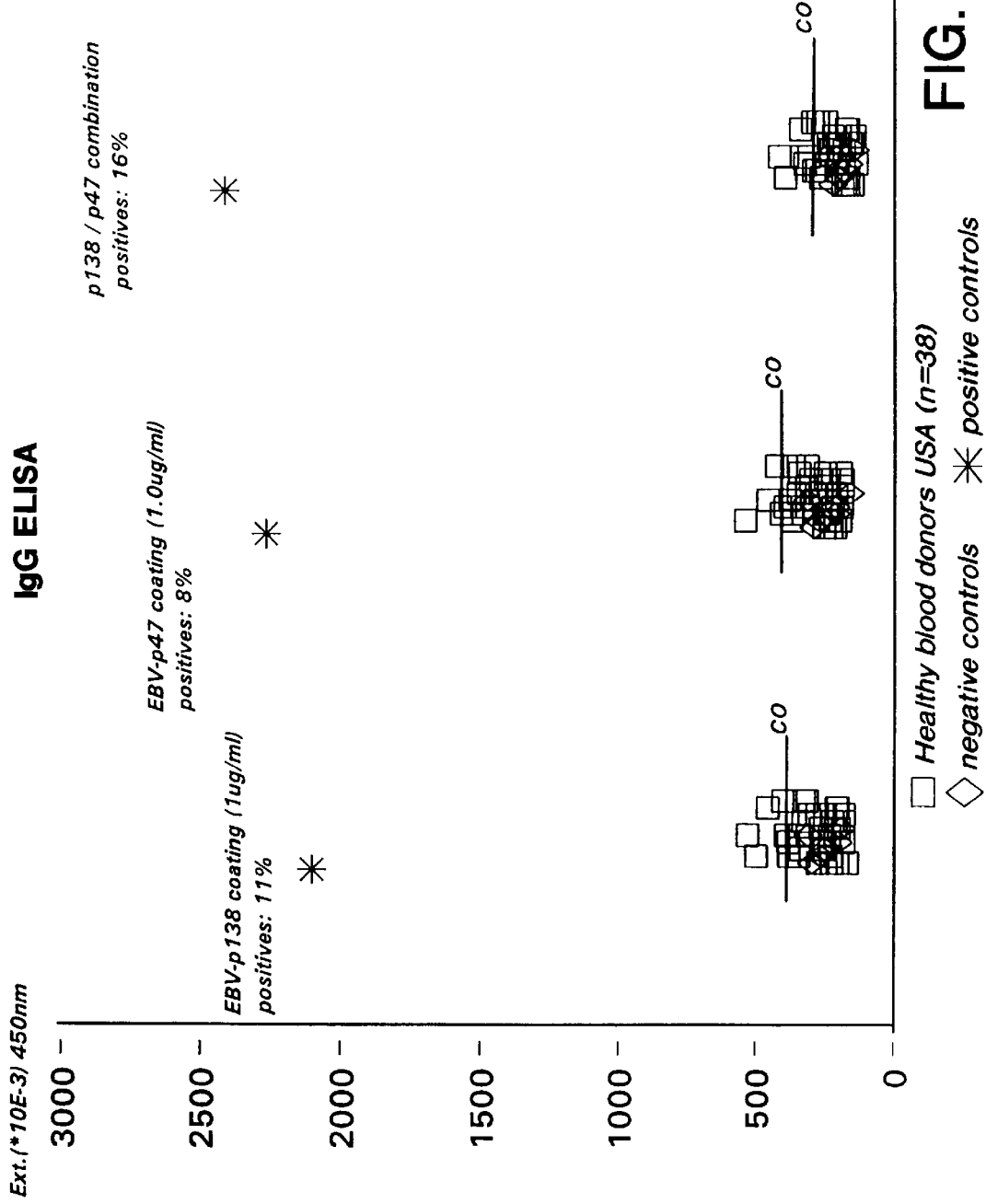

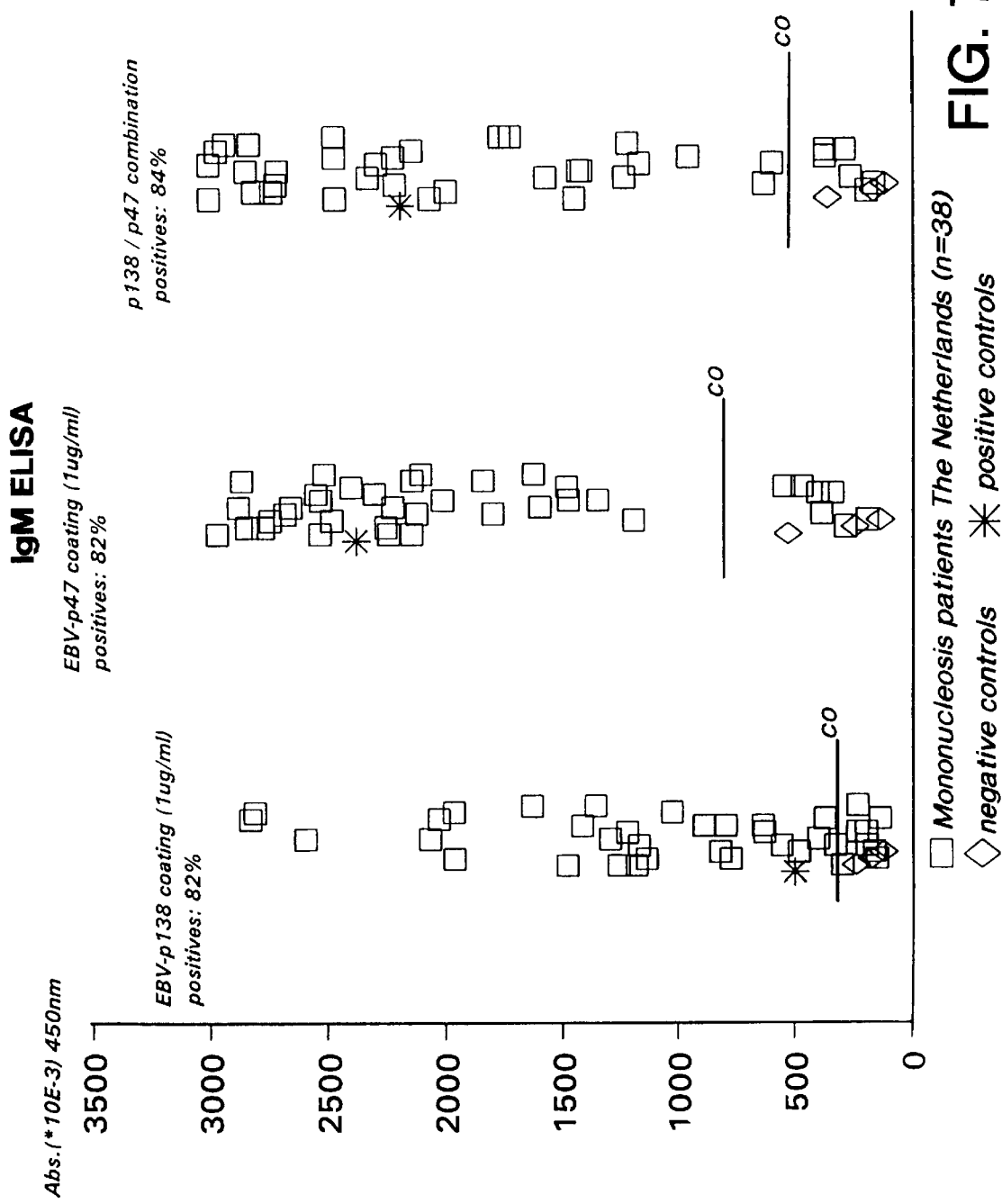

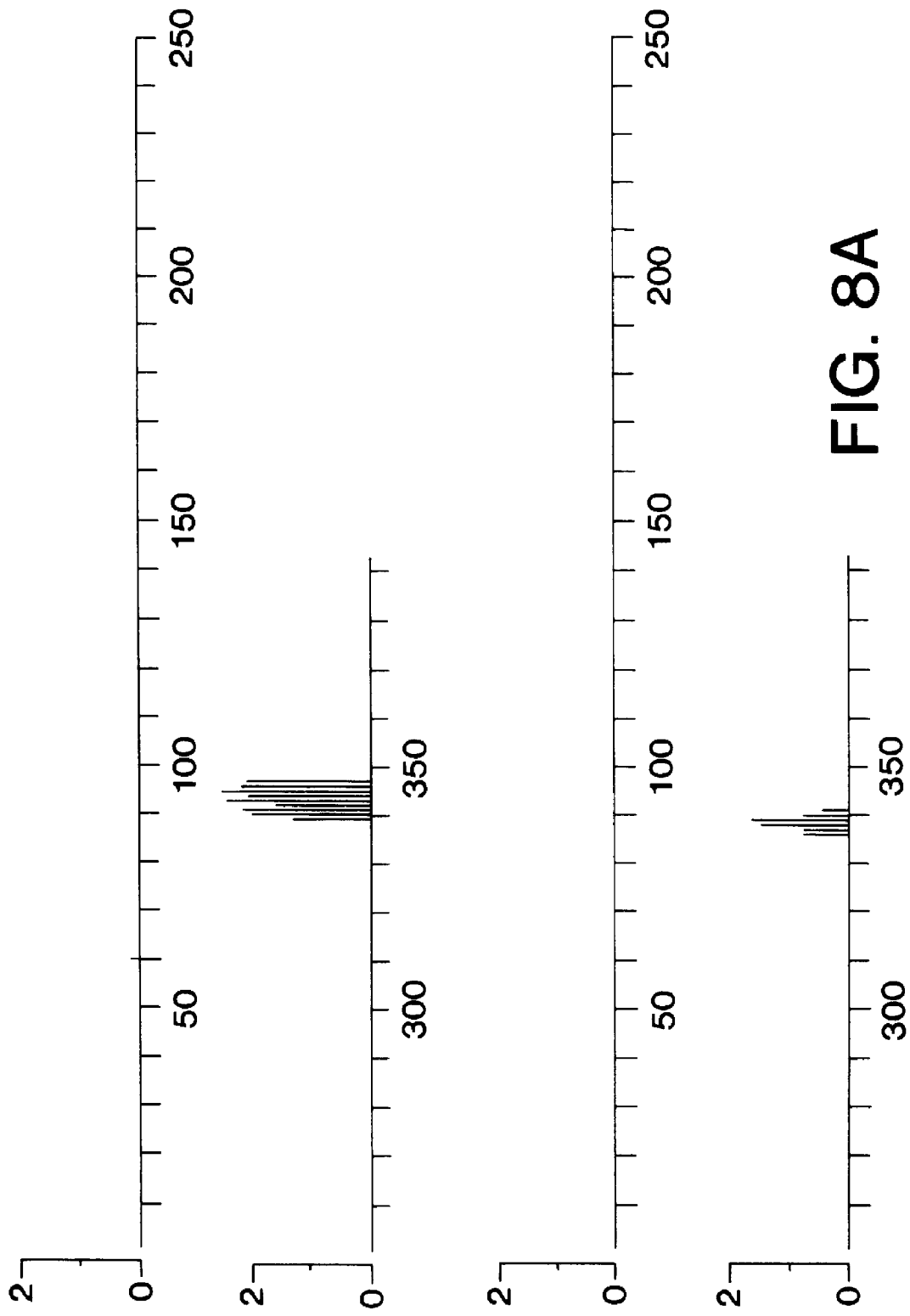

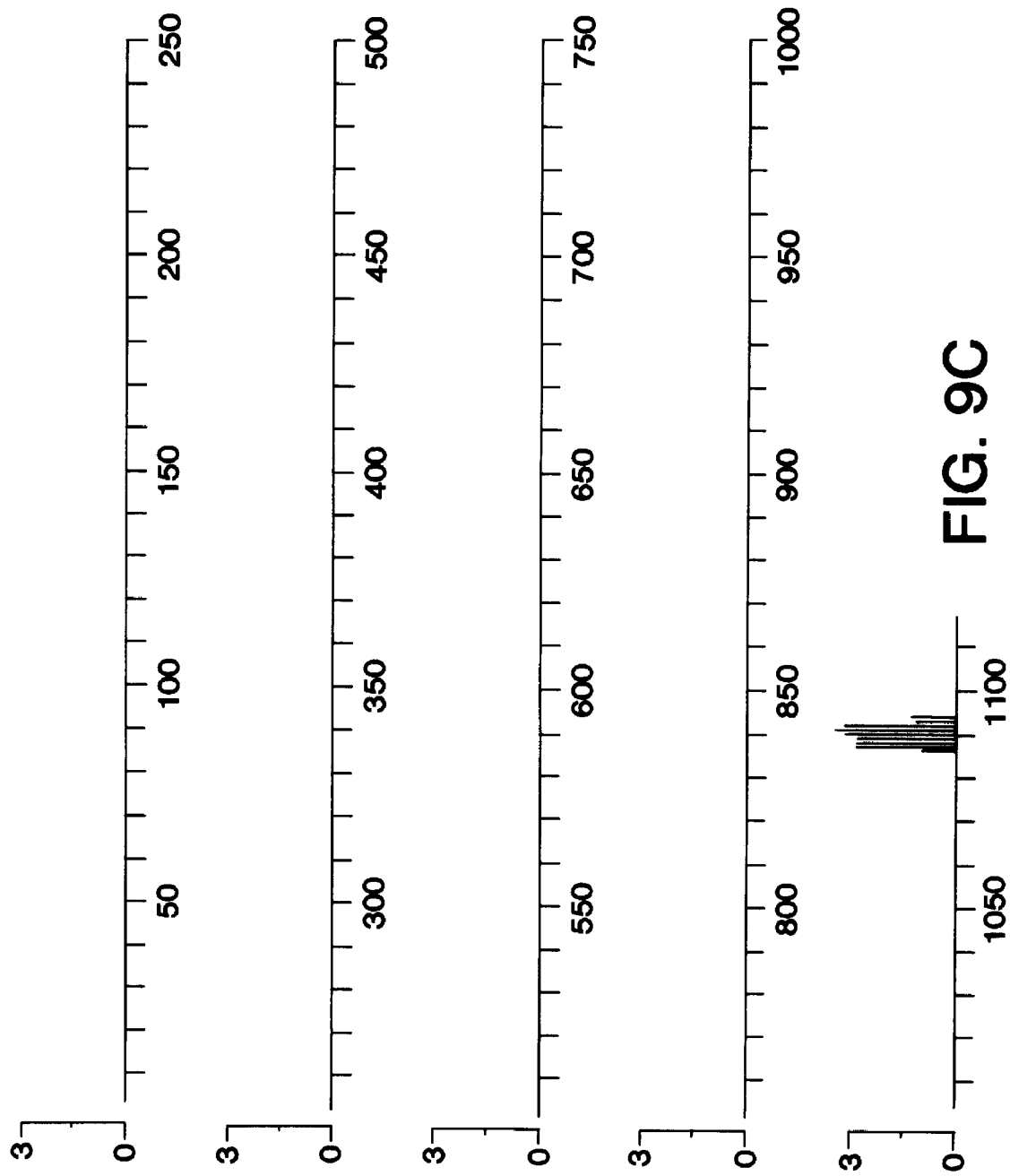

EPSTEIN-BARR VIRUS PEPTIDES AND ANTIBODIES AGAINST THESE PEPTIDES

FIELD OF THE INVENTION

The present invention relates to peptides immunochemically reactive with antibodies to the Epstein-Barr virus (EBV), (monoclonal) antibodies against these peptides, and cell lines capable of producing monoclonal antibodies. The invention is further concerned with immunological reagents and methods for the detection of EBV or antibodies directed against EBV.

BACKGROUND OF THE INVENTION

Epstein-Barr Virus (EBV) is an ubiquitous human herpes virus that was first discovered in association with the African (endemic or e) form of Burkitt's lymphoma (BL). Subsequently the virus was also found associated with nasopharyngeal carcinoma (NPC) and was shown to be the causative agent of infectious mononucleosis (IM). Infection usually occurs during early childhood, generally resulting in a subclinical manifestation, occasionally with mild symptoms. Infection during adolescence or adulthood, however, can give rise to IM characterized by the presence of atypical lymphocytes in the periphery. The bulk of these lymphocytes are T lymphocytes; however, included in their number are a small population of B lymphocytes infected by EBV. The infection of B lymphocytes may also be accomplished in vitro. Such cells become transformed and proliferate indefinitely in culture and have been referred to as "immortalized", "latently infected" or "growth transformed". As far as is known, all individuals who become infected with EBV remain latently infected for life. This is reflected by the lifelong continuous presence of small numbers of EBV-genome positive transformed B-cells among the circulating peripheral blood lymphocytes and the continuous but periodic shedding of virus in the oropharynx.

In the vast majority of cases EBV infection results in a lymphoproliferative disease that may be temporarily debilitating, but is always benign and self-limiting. In certain immunosuppressed individuals, however, the result can be full-blown malignancy. This occurs in individuals who are immuno-suppressed intentionally, particularly children receiving organ transplants who are treated with cyclosporine A, or opportunistically, as in the case with individuals infected with HIV, or genetically, as in the case of affected males carrying the XLP (x-linked lymphoproliferative syndrome) gene. In these cases the resulting malignancies derive from the polyclonal proliferation of EBV-infected B cells. In addition, in such patients uncontrolled epithelial replication of the virus is detectable in lesions of oral hairy leukoplakia. Thus, the immune response plays a central role in the control of EBV infection.

As mentioned above EBV is a member of the herpesviruses. It possesses the following structural properties:

The EBV genome consists of a linear double stranded DNA molecule (172,000 basepairs).

The virion consists of a core (proteins and DNA), surrounded by an icosahedral capsid, and a membrane envelope enclosing the capsid. The icosahedral capsid is built up of hexameric and pentameric capsomeres. The membrane envelope consists of a protein/lipid bilayer membrane with spikes on its outer surface. The space between the capsid shell and the envelope is filled with amorphous protein, called the tegument.

Like all herpesviruses, EBV is capable of establishing a latent life-long infection in its host subsequent to primary infection. This latency represents a perfect balance between EBV and its human host, controlled by the hosts immune system.

To date most biochemical and biological studies have been performed on three prototype strains of EBV, being B95-8 (transforming virus produced in a marmoset cell line), P3HR1 (non-transforming virus produced by a Burkitt's lymphoma tumor cell line) and Raji (latent virus in a Burkitt's lymphoma tumor cell line).

During the last few years the entire DNA sequence of prototype virus strain, B95-8, has been determined. Analysis of this sequence has resulted in the identification of more than 80 open reading frames (Baer et al., 1984, Nature 310, p. 207–211).

The biology of EBV poses a special problem to investigators because its biological characteristics (latent infection) do not lend itself to the classic virus analysis. Furthermore, its cell and host range are effectively limited to human (and those of a few higher primates) B-lymphocytes and epithelial cells which are generally not amenable to culture in vitro. In addition, the absence of a fully permissive cell type, one in which the virus lytically replicates, has severely limited the ability to produce large amounts of the virus.

DNA molecules of B95-8, P3HR1- and Raji-isolates have been the prototypes for detailed restriction endonuclease mapping, and for cloning into *Escherichia coli* (*E. coli*) plasmids and in bacteriophage lambda, and for nucleotide sequencing.

The EBV-genome consists of a single double stranded DNA molecule build-up with unique and tandemly repeated DNA-elements. Each end of the DNA molecule contains multiple terminal sequences which permit covalently linking and circularization of the genome. In virus particles the EBV-genome is only detectable in a linear form. On the contrary, it exists as a circular episome inside the nucleus of latently infected cells, and occasionally becomes integrated into the host cell chromosomes.

The internal repeat sequences, IR1 to IR4, separate the EBV-genome into 5 unique regions. The U2 and U3 regions vary extensively among different EBV isolates and, the former being almost entirely deleted in the P3HR-1 strain of EBV.

The nomenclature for EBV reading frames is based on their position in the virus genome. The names begins with the initials of the BamH1 or EcoR1 restriction fragment where expression begins. The third letter in the name is L or R, depending or whether the expression is leftward or rightward on the standard map. (So BLLF2 is the second leftward reading frame starting in BamH1 restriction fragment L.).

The serological classification of virus antigens in the production cycle of EBV is based on different fluorescence techniques.

Antigens specifically detected by means of the anti-complement immunofluorescence technique in the nucleus of fixed latently infected B-cells (e.g. Raji-cells) are classified as Epstein-Barr nuclear antigens (EBNA).

Upon activation of viral gene expression by chemical or viral factors a class of early antigens (EA) is detected whose synthesis is not blocked by inhibition of viral DNA synthesis. Dependent on the type of fixative used (Methanol or Acetone) two distinct sets of EA are detectable, $EA_R$ and $EA_D$. EA is detectable by indirect immunofluorescence in the cytoplasm and nucleus of induced cells. Following onset of viral DNA-synthesis (and depending upon it) virus structural proteins (VCA) are synthesized which are detectable by indirect immunofluorescence in the cytoplasm and nucleus of virus producer cells (e.g. $P_3HR_1$ cells). On the surface of viable infected cells, induced for virus production a set of antigens (MA) is detectable by indirect immunofluorescence. These antigens can also be found on the viral envelope and are important targets for virus neutralization.

Detection of EBV-specific antibodies in human sera can routinely be performed by serological techniques as described by Henle and Henle (Human Pathology, 5, 551–565, 1974).

Based upon biochemical and immunofluorescence data it is possible to distinguish five different classes of antigen molecules. The different viral polypeptides are designated by their molecular weight, and no common nomenclature has been established for all EBV-proteins in order to allow their unique description.

The five different groups of antigens are:
A. The group of antigens which are expressed during a state of latency (EBNAs and LMPs).
B. The group of antigens which are responsible for genome activation and initial induction of viral replication (IEA).
C. The group of antigens which are induced by IEA-gene products and which are required for replication of viral DNA; these antigens are mostly viral enzymes (EA).
D. The group of antigens which are structural components of the viral particle and are expressed late in the viral replication cycle (VCA), after initiation of viral DNA-synthesis.
E. The group of antigens which are expressed in the cell membrane of the infected cell (MA).

Epstein-Barr Early Antigens (EBV-EA)

EBV-early antigens (EA) are expressed in EBV-producer cells before onset of viral DNA-synthesis and can be studied specifically when such producer cells are treated with inhibitors of viral DNA polymerase (e.g. phosphonoacetic acid). Alternatively EA can be detected in cells abortively infected with EBV or in non-producer lymphoblastoid cells (e.g. Raji cells) activated with chemicals such as IUdR or BUdR, or TPA and butyrate.

The EA antigens represent a group of viral proteins required for both shutdown of host macromolecular synthesis and initiation of viral DNA-synthesis.

Although the exact nature of all EA-complex proteins is not known to date, some of its components have been defined molecularly in recent years.

By immunofluorescence (IF) analysis using both human sera and monoclonal antibodies two sets of Early Antigens are described which differ in their sensitivity to fixatives such as acetone and methanol. One IF-pattern is the diffuse type (D), with staining of both the nucleus and the cytoplasm, whereas the other is restricted (R) to filamentous material in the cytoplasm only. It is found that the R component is destroyed by methanol or ethanol fixation but resistant to acetone, whereas the D component is resistant to these fixatives.

The EA-D complex is composed at least of the following EBV-genome encoded proteins, P47-54 (BMRF1) the DNA-polymerase associated protein, P138 (BALF2) the major DNA binding protein, p110 (BALF5) the DNA-polymerase, p55 (BGLF5) the alkaline DNAse, P65 (BXLF1) the thymidine kinase and P52 (BMLF1) the early transactivator.

The EA-R complex is composed of at least the following EBV proteins, P85 (BORF2) the ribonucleotide reductase large subunit, p30 (BARF1) the RR small subunit and P17 (BHRF1) the Bcl-2 homologue.

Antibodies to EBV-EA complex proteins are generally detectable in patients with active (acute or chronic) EBV-infections, with anti-EA-R being more frequently detectable in apparently healthy blood donors.

Antibodies of IgG, IgM and IgA classes to EA-D complex proteins have been detected in acute phase of mononucleosis, with IgM and IgA disappearing more rapidly than IgG during convalescence. In (severe) chronic EBV infections high titers of IgG antibodies are found to both EA-D and EA-R complexes, with occasional IgA but no IgM. In Nasopharyngeal Carcinoma high titers of both IgG and IgA are found to EA-D, the latter being of diagnostic and prognostic importance for disease monitoring. In contrast, another EBV-associated malignancy, Burkitt Lymphoma, is frequently associated with high IgG titers to the EA-R component.

In the vast majority of cases the antibody responses described above have been studied using indirect immunofluorescence techniques on different EBV cell lines induced for EA expression and fixed with acetone or methanol. More molecular defined serological studies have been started only recently.

At present, the underlying mechanism(s) of these different immune responses to EA-D and EA-R complexes is not defined, nor is it clearly defined which EA-D or EA-R proteins are detected by human antibodies in different EBV disease syndromes.

As mentioned above, some of the molecular characteristics of both EA-D and EA-R complex components have been described in some detail in recent years and their coding open reading frames have been located on the viral genome.

Production of these components from EBV-producer cells however is complex and gives low yields due to the low level of expression of these proteins in cell culture. This has prevented the development of more simple diagnostics as alternative to the laborious and subjective IF-based serological tests.

Expression of defined components in alternative host systems has been described, but their routine application in diagnostic tests requires high level of purification, in order to remove potentially interfering host proteins (e.g. E. coli).

At present EBV specific serodiagnosis is accomplished by rather subjective immunofluorescence tests. Progress to more simple and uniform diagnosis (e.g. ELISA) is hampered because bulk production and purification of viral antigens are not possible using standard virus producing cell lines.

The only way to achieve this would be to use alternatively prepared EBV antigen(s). These EBV antigens could be prepared with either genetic engineering techniques or synthetic peptide techniques.

For the development of a specific and sensitive method to enable a reliable diagnosis to be made in various phases of the infection with EBV it is of great importance to identify immuno-dominant viral proteins and epitopes thereof.

SUMMARY OF THE INVENTION

It has now been found that several immunoreactive (peptide) domains on EBV-EA(D) P47-54 (BMRF1) are localized in the C-terminal region of the protein by using patient sera, though some individuals also have antibodies to domains elsewhere in the protein (FIG. 1).

Immunoreactive (peptide) domains on EBV-EA(D) P138 (BALF2) have been located at multiple sites on the protein, mostly confined to amino acid sequence 490-600 and to the C-terminus at amino acid sequence 1000-1128 (FIG. 2).

Defining synthetic peptide fragments, representing immunodominant domains of EA-proteins, capable of replacing the intact proteins in diagnostic tests, is a subject of the present invention.

Synthetic peptides have the advantage of being chemically well defined, thus allowing easy and reproducible production at high yields, well suited for application in diagnostic assays which can be manufactured and used with greater reproducibility.

DETAILED DESCRIPTION OF THE INVENTION

The present invention provides peptides, immunochemically reactive with antibodies to the Epstein Barr Virus, comprising at least part of the EA-p47-54 protein which comprises at least part of the amino acid sequence as shown in SEQ ID No.: 1, 2, 4, or 5.

Furthermore, the present invention provides peptides, immunochemically reactive with antibodies to the Epstein Barr Virus, comprising at least part of the EA-p47-54 protein which comprises at least part of the amino acid sequence as shown in SEQ ID No.: 4 linked to at least part of the amino acid sequence as shown in SEQ ID No.: 5.

An object of the present invention are peptides comprising at least part of the amino acid sequence as shown in SEQ ID No.: 6.

Also the present invention provides peptides, immunochemically reactive with antibodies to the Epstein Barr Virus, comprising at least part of the EA-p138 protein, which comprises at least part of the amino acid sequence as shown in SEQ ID No.: 7, 8, 9, or 10.

In contrast to the natural EBV, the peptides according to the invention have the great advantage that these are of a safe non-infectious origin.

The peptides and fragments thereof according to the invention are found to be particularly suitable for use in a diagnostic method for the determination of the presence of EBV or EBV-antibodies in a sample. Moreover, peptides and fragments thereof according to the invention may be used in suitable pharmaceutical dosage forms in the treatment of an EBV-related disease. The preparation of vaccines thus obtained which contain a peptide or fragment thereof as active ingredients, is known to one skilled in the art.

The peptides according to the present invention incorporated in immunological reagents have improved reactivity and specificity (performance) compared with currently available EA(D) reagents.

Therefore the utilization of these immunological reagents in serological tests allows the development of assays that will permit a better differential diagnosis in patients with active EBV-infections.

Furthermore, object of the present invention is the finding that the presence of antibodies to the selected EA(D) peptides is correlated with active EBV-infection.

Selected domains from EBV-EA(D) P47-54 and EBV-EA (D) P138 can be utilized for the detection of antibodies in patients with active EBV-infections. Such antibodies are virtually absent in healthy individuals.

The latter is further demonstrated by analysing the sera of healthy EBV-seropositive donors from different parts of the world for IgG reactivity to peptides from EA(D) p47-54 and P138 (FIG. 5).

From this figure it can be concluded that healthy EBV-seropositive donors with a (non-symptomatic) latent EBV infection rarely have antibodies to the selected EA(D) peptides. If these antibodies are detectable, the reactivity is low if compared to patients with active EBV-infections.

Another object of the present invention is the finding that the peptides according to the invention can be used either alone or in combination to detect IgG, IgM and IgA antibody subclasses to EA(D) in different EBV diseases.

Detection of EBV-VCA and EBV-EA(D) reactive IgM antibodies in the sera of infectious mononucleosis (IM) patients is indicative for the acute and early convalescence stage of infection and is therefore an important diagnostic parameter. IgG anti-EA(D) antibodies are present temporaly during the acute stages of IM and decrease during convalescence to low or undetectable levels. IgG-EA(D) may reappear in a selected group of patients with chronic or reactivated EBV-infections as well as patients with EBV-malignancies. Therefore the presence of IgG anti-EA(D) is useful as a marker for the diagnosis of (re)active EBV infection in a variety of clinical settings.

Finally the detection of IgA anti-EA(D) is linked to certain EBV-associated malignancies and has been proven to be of diagnostic and prognostic value in nasopharyngeal carcinoma.

The term "peptide" as used herein refers to a molecular chain of amino acids with a biological activity, and does not refer to a specific length of the product. Thus inter alia, proteins, fusion-proteins or -peptides oligopeptides and polypeptides are included.

If required peptides according to the invention can be modified in vivo or in vitro, for example by glycosylation, amidation, carboxylation or phosphorylation. Functional variants like, for example, acid addition salts, amides, esters, and specifically C-terminal esters, and N-acyl derivatives of the peptides according to the invention are therefore also considered part of the present invention. It will be understood that for the particular proteins or polypeptides embraced herein, natural variations can also exist. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous proteins.

The term "at least a part of" as used herein means an amino acid sequence comprising a subsequence of a peptide of the invention. Said part or fragment is a peptide having one or more immunogenic determinants of the EBV-EA protein. Fragments can inter alia be produced by enzymatic cleavage of precursor molecules, using restriction endonucleases for the DNA and proteases for the polypeptides. Other methods include chemical synthesis of the fragments or the expression of peptide fragments by DNA fragments.

Suitable immunogenic fragments of a peptide according to the invention containing (an) epitope(s) can be found by means of the method described in patent application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on the so-called pepscan method, wherein a series of partially overlapping peptides corresponding with partial sequences of the complete polypeptide under consideration, are synthesized and their reactivity with antibodies is investigated.

In addition, a number of regions of the peptides can be designated epitopes on the basis of theoretical considerations, although the predictive value of these theoretical considerations is limited. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

The preparation of the peptides or fragments thereof according to the invention is effected by means of one of the known organic chemical methods for peptide synthesis or with the aid of recombinant DNA techniques.

The organic chemical methods for peptide synthesis are considered to include the coupling of the required amino acids by means of a condensation reaction, either in homogeneous phase or with the aid of a so-called solid phase.

The condensation reaction can be carried out as follows:
a) condensation of a compound (amino acid, peptide) with a free carboxyl group and protected other reactive groups with a compound (amino acid, peptide) with a free amino group and protected other reactive groups, in the presence of a condensation agent;
b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of above-mentioned peptides according to the invention using the "solid phase method" is for instance described in J. Amer. Chem. Soc. 85, 2149 (1963) and Int. J. Peptide Protein Res. 35, 161–214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine-function.

A particularly suitable solid phase is, for example, the p-alkoxybenzyl alcohol resin (4-hydroxy-methyl-phenoxy-methyl-copolystrene-1% divinylbenzene resin), described by Wang (1974; J. Am. Chem. Soc. 95, 1328). After synthesis the peptides can be split from this solid phase under mild conditions.

After synthesis of the desired amino acid sequence, detaching of the peptide from the resin follows, for example, with trifluoromethane-sulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzene-sulphonyl or p-toluene-sulphonyl group, but other groups can also be used, such as substituted or unsubstituted aryl or aralkyl groups, for example benzyl and triphenylmethyl, or groups such as ortho-nitrophenyl-sulphenyl and 2-benzoyl-1-methyl-vinyl. A particularly suitable α-amino-protective group is, for example, the base-sensitive 9-fluorenyl-methoxycarbonyl (Fmoc) group [Carpino & Han (1970) J. Amer. Chem. Soc. 92, 5748].

A more extensive account of possible protecting groups can be found in The Peptides, Analysis, Synthesis, Biology, Vol. 1–9 (Eds. Gross, Udenfriend and Meienhofer) 1979–1987 (Academic Press, Inc.).

It is necessary also to protect the ε-amino group of lysine and advisable for the guanidine group of arginine. Customary protective groups in this connection are a Boc-group for lysine and a Pmc- or Pms- or Mbs-group or Mtr-group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

The immunoreactive peptides according to the present invention can also be combined in a single molecule. The covalent linkage of two or more peptides in a hybrid- or combi-peptide can for instance be carried out through solid phase peptide synthesis, using the methods described above, of a peptide sequence wherein the amino acid sequences of the individual peptides are aligned. It is understood that a linker sequence may be inserted between the individual peptides sequences. Such a linker sequence may for instance be a stretch of 2–5 residues of glycine.

A hybrid- or combi-peptide can also be prepared through solid phase synthesis using the fragment condensation approach. The latter method, in which the fragments (the sequences of which may correspond with the sequences of the individual peptides of the invention) are seperately prepared and purified, is preferred in the synthesis of the longer hydrid- or combi-peptide sequences. The methodology for the preparation of longer peptides is known in the art, and for instance described in The Peptides, Analysis, Biology, Vol. 1–9 (vide supra).

Alternatively, hybrid- or combi-peptides can be prepared through conjugation of appropriately modified peptides of the present invention.

In a preferred method for the conjugation of two different peptide sequences which are devoid of the amino acid cysteine, the peptides are derivatized to contain an additional residue of cysteine at either the carboxyl- or the amino-terminal end. One of the peptides is subsequently activated at the single cysteine thiol function with 2,2'-dithiodipyridine. The resulting pyridyl-dithio-peptide derivative is then reacted with the second peptide containing the cysteine thiol group to yield a hybrid peptide in which the individual peptides are linked through a disulfide bond.

Numerous other methods for the preparation of hybrid peptides can be envisaged. Use can be made of the chemical methodology that has been developed in the field of protein-protein conjugation. An overview of such methods is given by Means and Feeney (Bioconj. Chem. 1, 2–12, 1990). For instance, the use of well known homo- or heterobifunctional cross-linking agents allow the coupling of individual peptides through a disulfide bond, or a thioether or amide bond, or the like.

As already indicated above, the peptides according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide or as a fusion protein with, for example, (part of) β-galactosidase. This type of peptides therefore likewise falls within the scope of the invention. For this purpose, as a constituent of a recombinant DNA, a nucleic acid sequence is used which codes for a peptide according to the invention and which, furthermore, is substantially free from nucleic acid segments, which in the naturally occurring EBV genome flank the nucleic acid sequence indicated above.

This latter method involves the preparation of the desired peptide by means of bringing to expression a recombinant polynucleotide with a nucleic acid sequence which is coding for one or more of the peptides in question in a suitable micro-organism as host.

A nucleic acid sequence encoding a peptide according to the present invention can be ligated to various replication effecting DNA sequences with which it is not associated or linked in nature resulting in a so called recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences are known in the art and include inter alia plasmid vectors such as pBR322, the various pUC, pGEM and Bluescript plasmids, bacteriophages, e.g. kgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule are known to those of ordinarily skill in the art and are inter alia set forth in Maniatis, T. et al. (Molecular Cloning A Laboratory Manual, second edition; Cold Spring Harbor Laboratory, 1989).

For example, the insertion of the nucleic acid sequence encoding a peptide according to the invention into a cloning vector can easily be achieved when both the genes and the desired cloning vehicle have been cut with the same restriction enzyme(s) as complementary DNA termini are thereby produced.

The recombinant vector molecules may additionally contain one or more marker activities that may be used to select for desired transformants, such as ampicillin and tetracycline resistance in pBR322, as for example ampicillin resistance and α-peptide of β-galactosidase in pUC8.

It should, of course, be understood that the nucleotide sequences inserted at the selected site of the cloning vector may include only a fragment of the complete nucleic acid sequence encoding for the peptides according to the invention as long as the transformed host will produce a polypeptide having at least one or more immunogenic determinants.

Antibodies, directed to a peptide according to the invention are also part of the present invention.

The peptides or fragments thereof prepared and described above can be used to produce antibodies, both polyclonal and monoclonal. Monoclonal antibodies directed against peptides according to the invention can be readily produced by one skilled in the art.

The monoclonal antibodies according to the present invention, therefore, provide a new means for the diagnosis of EBV infection.

Preferred antibodies according to the invention are monoclonal antibodies which bind to an epitope of the EBV-EA p47-54 protein, which epitope is recognized by monoclonal antibodies produced by the hybridoma cell lines deposited with the European Collection of Animal Cell Cultures (ECACC), Porton Down (UK), under deposit No. 95051619, 95051620, 95051621 and 95051622.

New (monoclonal) antibodies according to the invention, which are designated as EBV.OT13B, EBV.OT13D, EBV.OT14E, and EBV.OT13N were generated by immunizing mice with EBV-producer cell derived EBV-EA proteins.

Immortalized cell lines capable of excreting monoclonal antibodies according to the invention are also part of the present invention.

The preparation of cell lines producing monoclonal antibodies may occur by, for example, by the Kohler and Milstein technique (Kohler and Milstein devised the techniques that resulted in the formation monoclonal antibody-producing hybridomas (G. Kohler and C. Milstein, 1975, Nature 256:495–497; 1976, Eur. J. Immunol. 6:511–519)), transformation with Epstein-Barr Virus, or a direct transformation technique of B-lymphocytes with oncogenic DNA, or a direct fusion of human B-lymphocytes with a fusion partner being either a human or a mouse-human hybrid myeloma cell line, or a direct fusion of an EBV-transformed B cell line with said myeloma cell lines.

Preferred cell lines according to the invention are the cell lines deposited at the European Collection of Animal Cell Cultures, Porton Down (UK) under deposit No. 95051619, No. 95051620, No. 95051621, and No. 95051622.

These hybridoma cell lines were produced by the fusion of a myeloma cell with a lymphocyte derived from a mouse previously inoculated with EBV-producer cell derived EBV-EA proteins.

Monoclonal antibodies to proteins of the EBV-EA(D) complex are useful tools for the detection of EA(D) expression in cells and cell extracts both in vivo and in vitro, for purification purposes and for a variety of biochemical and immunological analysis techniques to study the function of these proteins.

Monoclonal antibodies have been raised to EBV-EA proteins and were found to react with epitopes within the selected peptide domains of the BMRF1 encoded EA(D) protein P47-54.

The binding domains on the P47-54 protein for two of these monoclonal antibodies, designated EBV.OT13N and EBV.OT14E, have been mapped to AA position 340-346 and 346-350 respectively (FIG. 8A).

Such antibodies can be used to detect the intact phosphorylated and non-phosphorylated forms of the BMRF1 encoded P47-54 protein, which is expressed in productively infected cells (FIG. 8B, lane VCA and EA) but not in latently infected cells (FIG. 8B, lane X50/7). The antibodies are specific for EBV P47-54 and do not cross-react with cellular components in EBV negative cells (FIG. 8B, lane BJAB).

Monoclonal antibodies have been raised to EBV-EA proteins and were found to react with epitopes within the selected peptide domains of the BALF2 encoded EA(D) protein P138.

The binding domains on the P138 protein for two of these monoclonal antibodies, designated EBV.OT13B and EBV.OT13D, have been mapped to AA position 515-521 and 1092-1098 respectively (FIG. 9A).

Such antibodies can be used to detect the intact form of BALF2 encoded P138 protein, which is expressed in productively infected cells (FIG. 9B, lanes VCA and EA) but not in latently infected cells (FIG. 9B, lane X50/7). The antibodies are specific for EBV P138 and do not cross-react with cellular components in EBV-negative cells (FIG. 9B, lane BJAB).

The invention further comprises the use of antibodies to said peptide in immunological and biochemical methods aiming to detect the full length protein in a test fluid or tissue specimen.

Prior to the present invention, detection of early antigens in EBV infected cells was performed by using the indirect immunofluorescence (IIF) technique using human sera as the anti EBV-EA antibody source. This is complicated by the false-positive and -negative reactions are frequently encountered.

The EBV.OT13B, 13D, 13N, 14E antibodies allows the sensitive detection of EBV-EA in a variety of EBV-infected cells by means of indirect immunofluorescence and similar techniques.

Antibodies, both monoclonal and polyclonal, directed against peptides according to the invention are very suitable in diagnosis and immunocytochemistry for detection in situ in tissue specimen, while those antibodies which are neutralizing are very useful in passive immunotherapy.

Part of the invention is also the "humanizing" of the monoclonal antibodies in question. Techniques for raising the "humanized" monoclonal antibodies are known in the art.

An immunochemical reagent comprising one or more peptides or antibodies according to the invention is also part of the present invention.

The term "immunochemical reagent" according to the invention usually consists of one or more peptides according to the invention and a suitable support or a labelling substance.

Supports which can be used are, for example, the inner wall of a microtest well or a cuvette, a tube or capillary, a membrane, filter, test strip or the surface of a particle such as, for example, a latex particle, an aldehyde particle (such as a ceramic magnetizable particle with active aldehyde surface groups), an erythrocyte, a dye sol, a metal sol or metal compound as sol particle, a carrier protein such as BSA or KLH.

Labelling substances which can be used are, inter alia, a radioactive isotope, a fluorescent compound, an enzyme, a dye sol, metal sol or metal compound as sol particle.

In a method for the detection of antibodies directed against EBV in a sample, an immunochemical reagent according to the invention is brought into contact with the sample. The presence of immune complexes formed between the peptide and antibodies in the sample is detected and by this detection the presence of EBV antibodies in the sample is known and can be determined quantitatively.

Depending on the nature and further characteristics of the immunochemical reagent the immunochemical reaction that takes place is a so called sandwich reaction, an agglutination reaction, a competition reaction or an inhibition reaction.

For the detection of EBV in a sample an immunochemical reagent according to the invention, containing one or more peptides according to the invention, can be brought into contact with the sample and anti-EBV after which the presence of immune complexes formed can be detected and, from this, the presence of EBV in a sample can be determined.

A particularly suitable method for the detection of EBV in a sample is based on a competition reaction between a peptide according to the invention provided with a labelling substance and an EBV antigen (present in the sample) whereby the peptide and the antigen are competing with the antibody directed against EBV attached to a solid support.

The invention further comprises a method for the detection of Epstein-Barr virus in a sample characterized in that an antibody according to the invention is brought into contact with a sample whereafter the presence of immune complexes formed is detected which is a measure for the presence of Epstein-Barr Virus in the sample.

A test kit according to the invention comprises as an essential constituent an immunochemical reagent as described above. Carrying out a sandwich reaction, for the detection of EBV antibodies the test kit may comprise, for example, the peptide according to the invention coated to a solid support, for example the inner wall of a microtest well, and either a labelled peptide according to the invention or a labelled anti-antibody.

For carrying out a competition reaction, the test kit may comprise a peptide according to the invention coated to a solid support, and a labelled antibody directed against EBV preferably a monoclonal antibody directed against said peptide.

In an agglutination reaction the test kit comprises an immunochemical reagent which may comprise a peptide according to the invention coated to particles or sols.

Another embodiment of a test kit is, for example, the use of a labelled peptide according to the invention as immunochemical reagent in a competition reaction with an EBV antigen to be detected for a binding site on the antibody directed against EBV, which is coated to a solid support.

BRIEF DESCRIPTION OF THE FIGURES

Peptide code definition:
496 (p47-54): SEQ.ID.1
497 (p47-54): SEQ.ID.2
498 (p47-54): SEQ.ID.3
499 (p47-54): SEQ.ID.4
500 (p47-54): SEQ.ID.5
501 (p47-54): SEQ.ID.6
G-34-R (p138): SEQ.ID.7
D-28-S (p138): SEQ.ID.8
A-27-G (p138): SEQ.ID.9
G-21-V (p138): SEQ.ID.10

JM and 219: Sera from healthy, seropositive, control donors for EBV

TR: Sera from healthy, seronegative, control donors for EBV

IM: Sera from mononucleosis patients.

RR: Sera from a severe chronic EBV-infection patient.

FIG. 4A: Detection of (IgG) antibodies to individual synthetic peptides representing combinations of immunoreactive domains of EA(D) P138. Peptide sequences are described in the identification list and represent P138 AA-positions as indicated.

JM and QCD219: Sera from healthy, seropositive, control donors for EBV

TR: Sera from healthy, seronegative, control donors for EBV

IM: Sera from mononucleosis patients.

RR: Sera from a severe chronic EBV-infection patient.

Figure 4B:
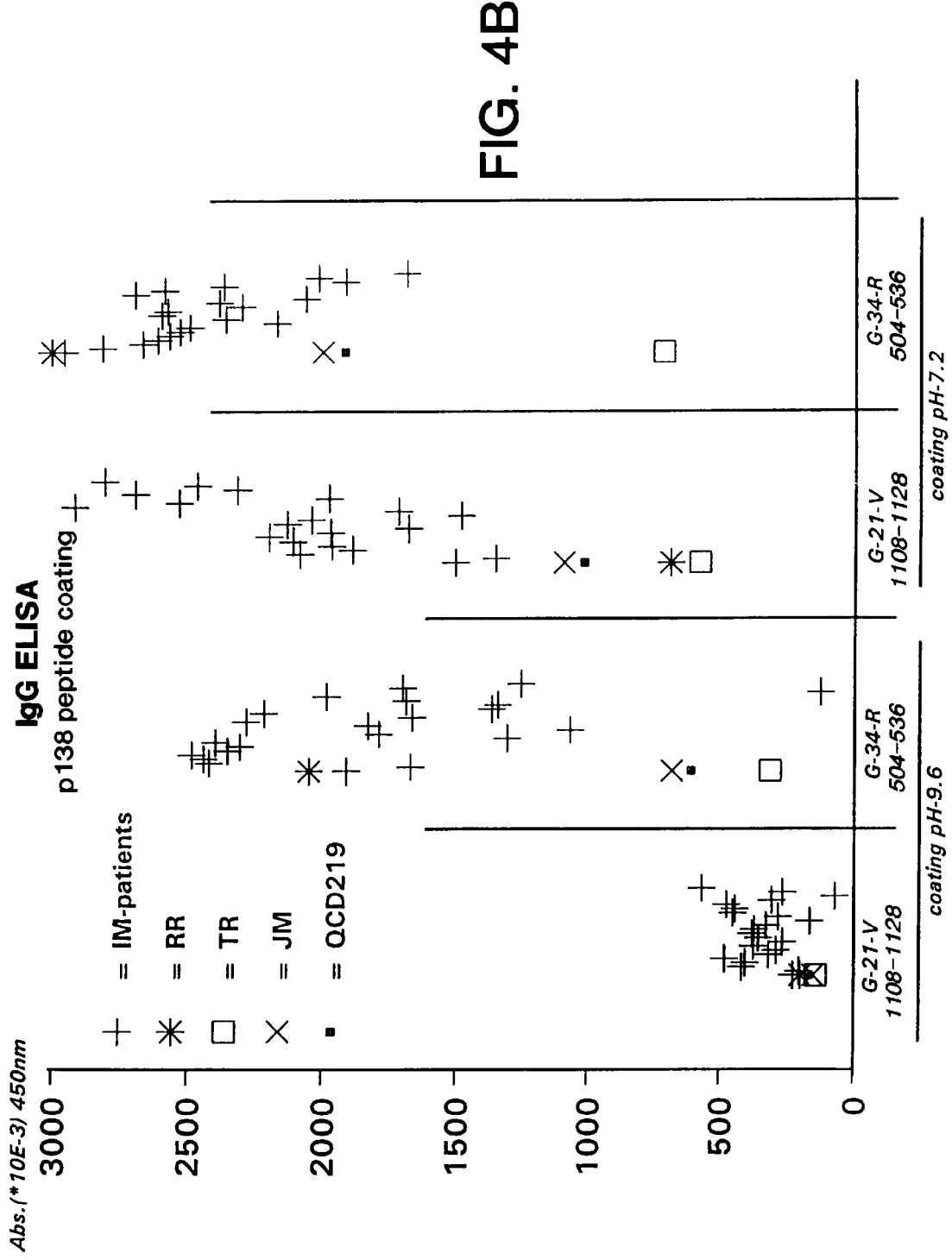

FIG. 4B: The same analysis as in FIG. 4A using P138-derived peptides G-21-V (SEQ.ID.10) and G-34-R (SEQ.ID.7) coated at pH 9.6 (0.1M carbonate buffer) or pH7.2 (0.1M phosphate buffer).

FIG. 5: Detection of (IgG) antibodies against individual components of the EA(D) complex or combinations thereof.

In this figure peptides #501 (P47-54; SEQ.ID.6) and G-34-R (P138; SEQ.ID.7) were coated separately or in a 1:1 combination directly onto the solid phase. Sera from 38 random mononucleosis patients were used at 1:100 dilution.

FIG. 6A & 6B: Detection of IgG antibodies to EBV-EA(D) using selected peptides from EA(D) P47-54 and P138 (i.c. #500 (SEQ.ID.5) and G-34-R (SEQ.ID.7) resp. or in a 1:1 combination) in healthy blood donor populations from Hong Kong (A) and the USA (B).

FIG. 7A: Detection of IgM antibodies against EBV-EA(D) P47-54 and P138 in sera of 38 mononucleosis patients using selected peptides (i.c. #501 (SEQ.ID.6) for P47-54 and G-34-R (SEQ.ID.7) for P138 separately coated onto the solid phase or coated in a 1:1 combination in the same well.

Figure 7B:
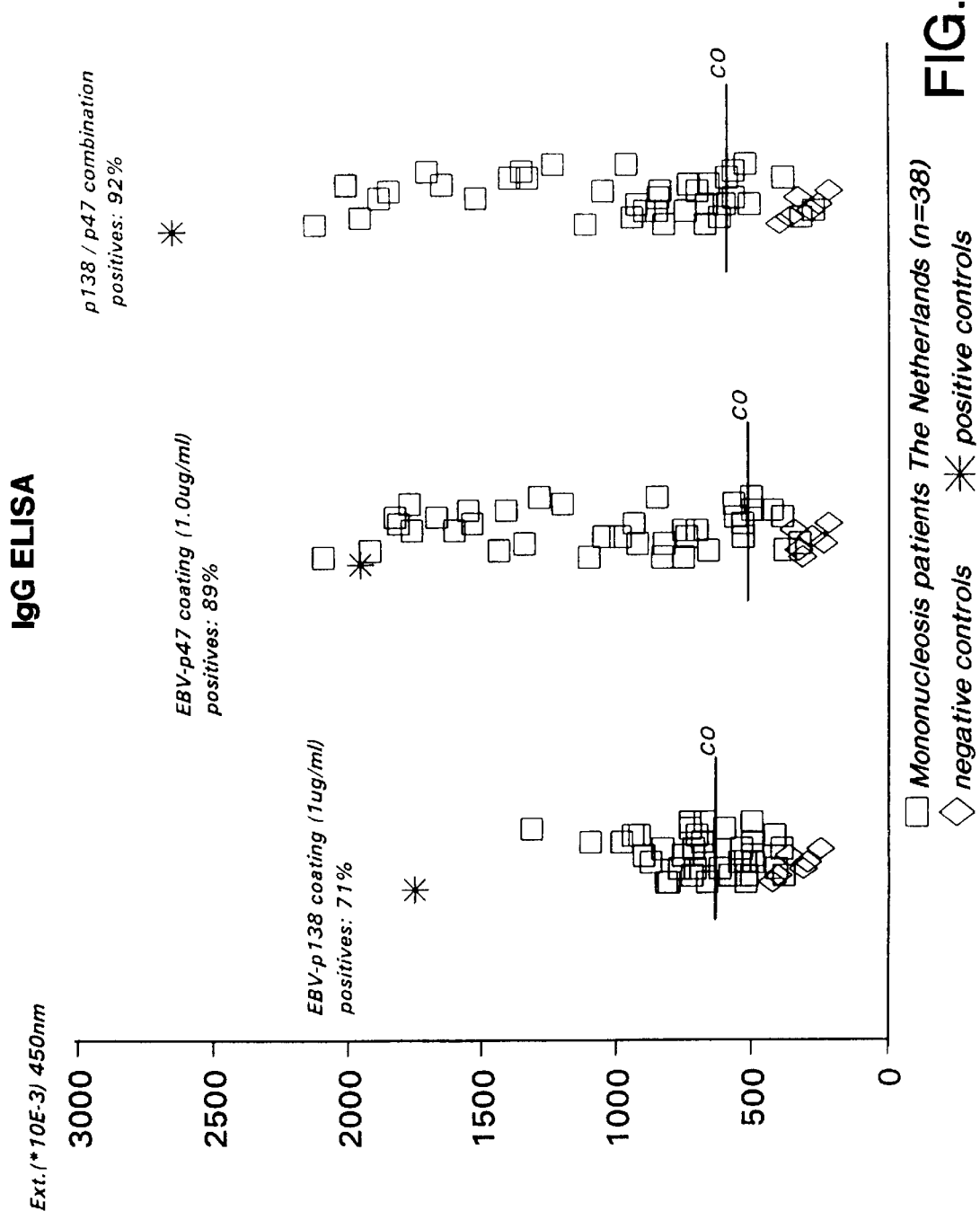

FIG. 7B: Detection of IgG antibodies with these reagents in sera from 38 mononucleosis patients.

Figure 7C:
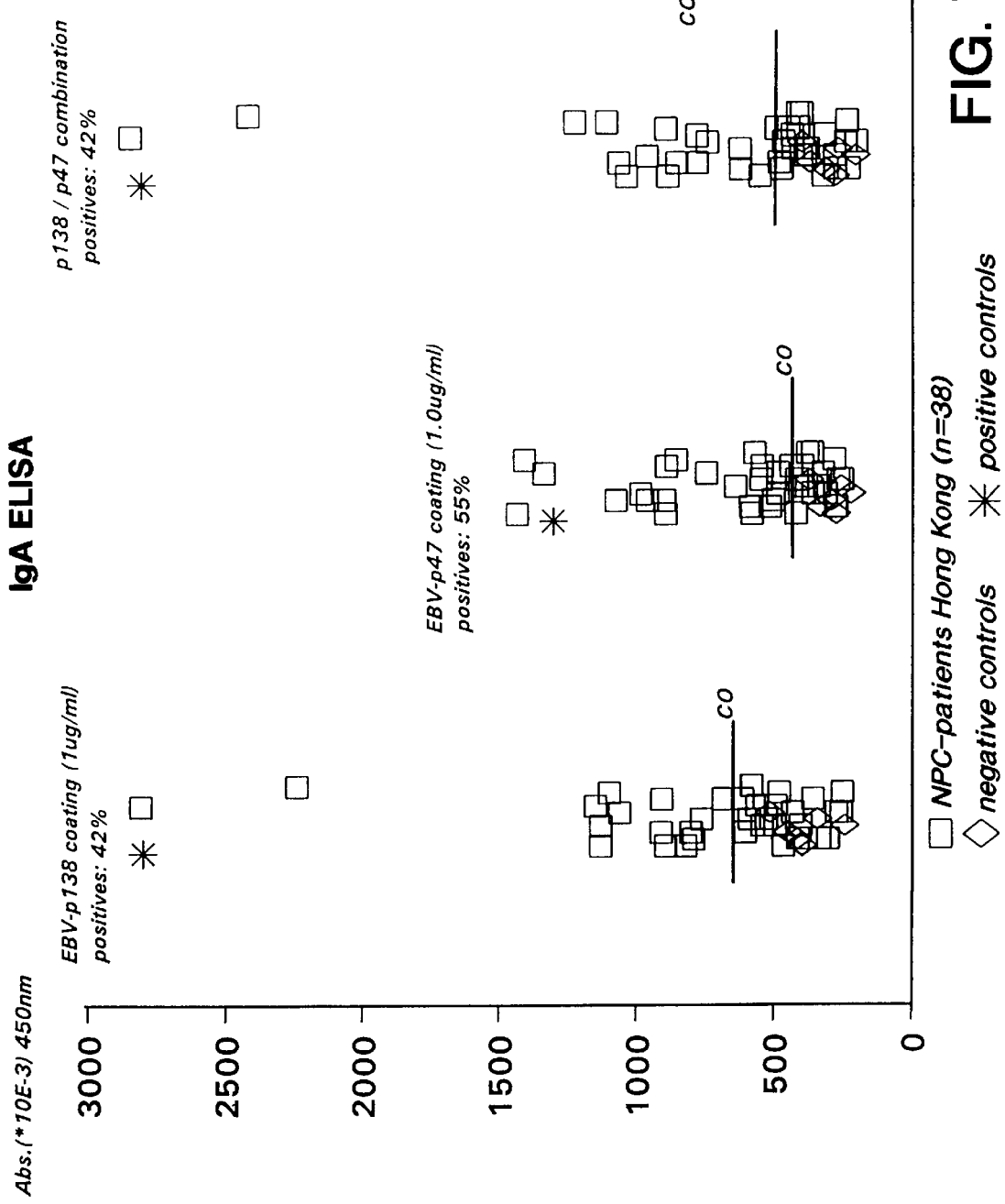

FIG. 7C: Detection of IgA antibodies with these reagents in sera from 38 nasopharyngeal carcinoma patients.

FIG. 8A: Identification of the binding domain of EBV.OT13N and EBV.OT14E on BMRF1-encoded EBV EA(D) P47-54 using the pepscan technique with overlapping 12-mer peptides.

Figure 8B:
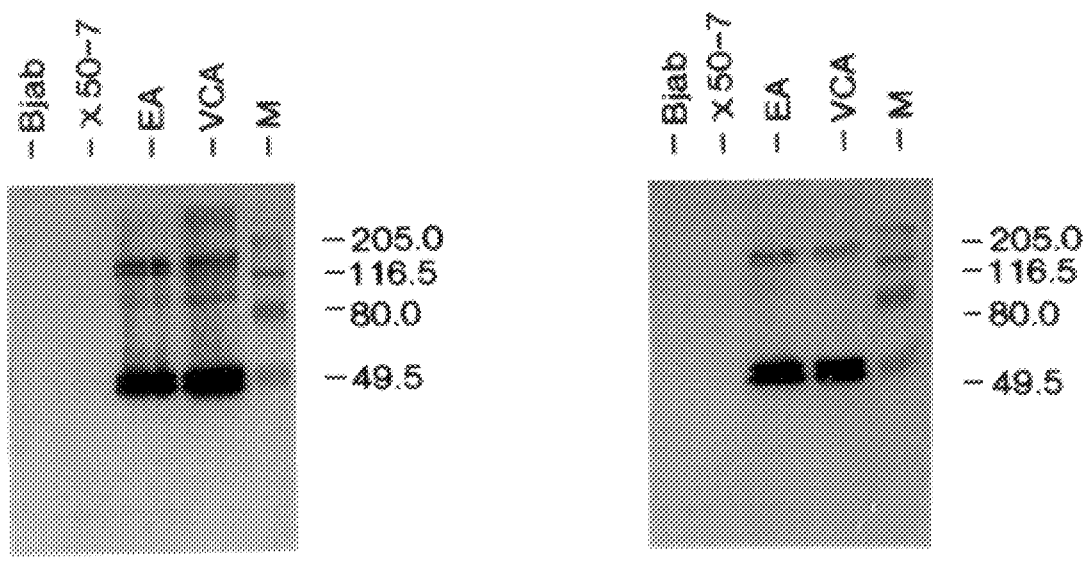

FIG. 8B: Immunoblot staining with EBV.OT13N and EBV.OT14E.

M=Molecular weight markers.

VCA=Nuclear extract of HH514 cells induced for expression of virus structural proteins.

EA=Nuclear extract of HH514 cells induced for expression of EA proteins by blocking viral DNA replication with PAA.

X50/7=Nuclear extract of X50/7 cells expressing only latent phase EBV-genes.

BJAB=Nuclear extract of EBV-negative Burkitt Lymphoma cell line BJAB.

Figure 9A:
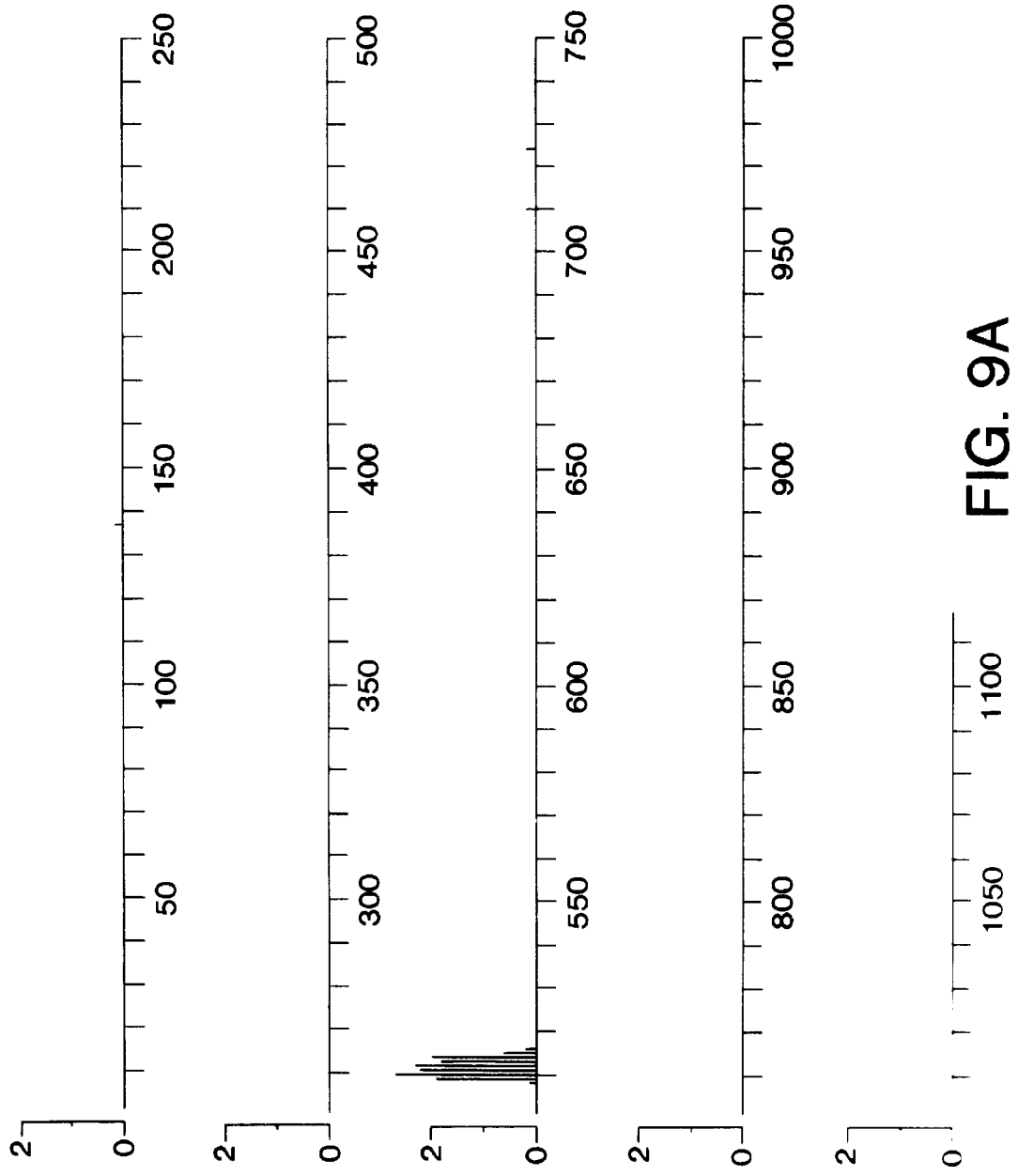

FIG. 9A: Identification of the binding domain of EBV.OT13B on BALF2-encoded EBV EA(D) P138 using the pepscan technique with overlapping 12-mer peptides.

Figure 9B:
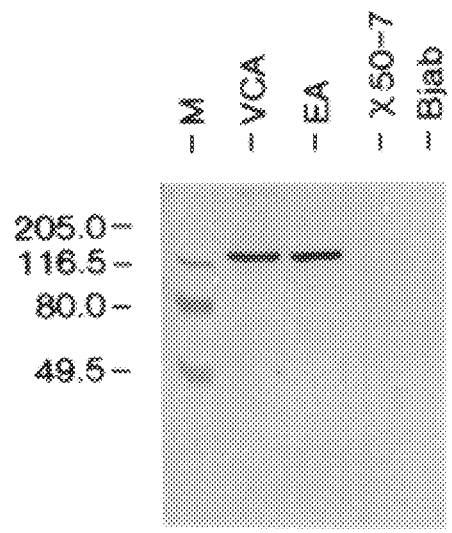

FIG. 9B: Immunoblot staining with EBV.OT13B.

M=Molecular weight markers

VCA=Nuclear extract of HH514 cells induced for expression of virus structural proteins.

EA=Nuclear extract of HH514 cells induced for expression of EA proteins by blocking viral DNA replication with PAA.

X50/7=Nuclear extract of X50/7 cells expressing only latent phase EBV-genes.

BJAB=Nuclear extract of EBV-negative Burkitt Lymphoma cell line BJAB.

FIG. 9C: Identification of the binding domain of EBV.OT13D on BALF2-encoded EBV EA(D) P138 using the pepscan technique with overlapping 12-mer peptides.

Figure 9D:
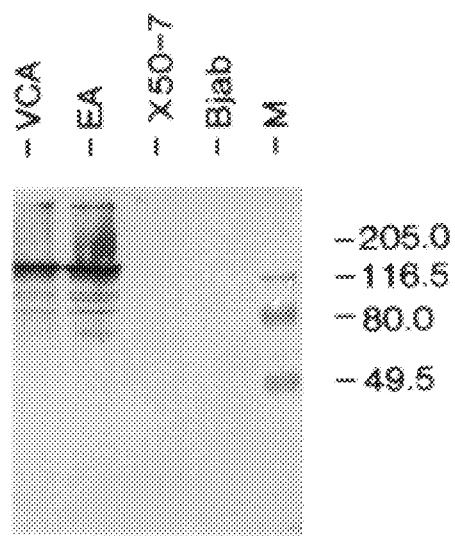

FIG. 9D: Immunoblot staining with EBV.OT13D.

M=Molecular weight markers

VCA=Nuclear extract of HH514 cells induced for expression of virus structural proteins.

EA=Nuclear extract of HH514 cells induced for expression of EA proteins by blocking viral DNA replication with PAA.

X50/7=Nuclear extract of X50/7 cells expressing only latent phase EBV-genes.

BJAB=Nuclear extract of EBV-negative Burkitt Lymphoma cell line BJAB.

The invention is further exemplified by the following examples:

EXAMPLES

Example 1

Localization of immunoreactive (peptide) domains on EBV-EA(D) P47-54 (BMRF1)

Peptides with a length of 12 amino acids (AA) and an overlap of 11 AA of the AA sequence of the complete BMRF1 reading frame were synthesized by automated solid phase peptide synthesis onto chemically activated pins as originally described by Geijsen et al (P.N.A.S., USA, 83 (1994) p.3998–4002).

The immunoreactivity for EBV-specific antibodies was determined as described by Middeldorp and Meloen (J.Virol.Meth. 21 (1988) p.147–159).

Figure 1:
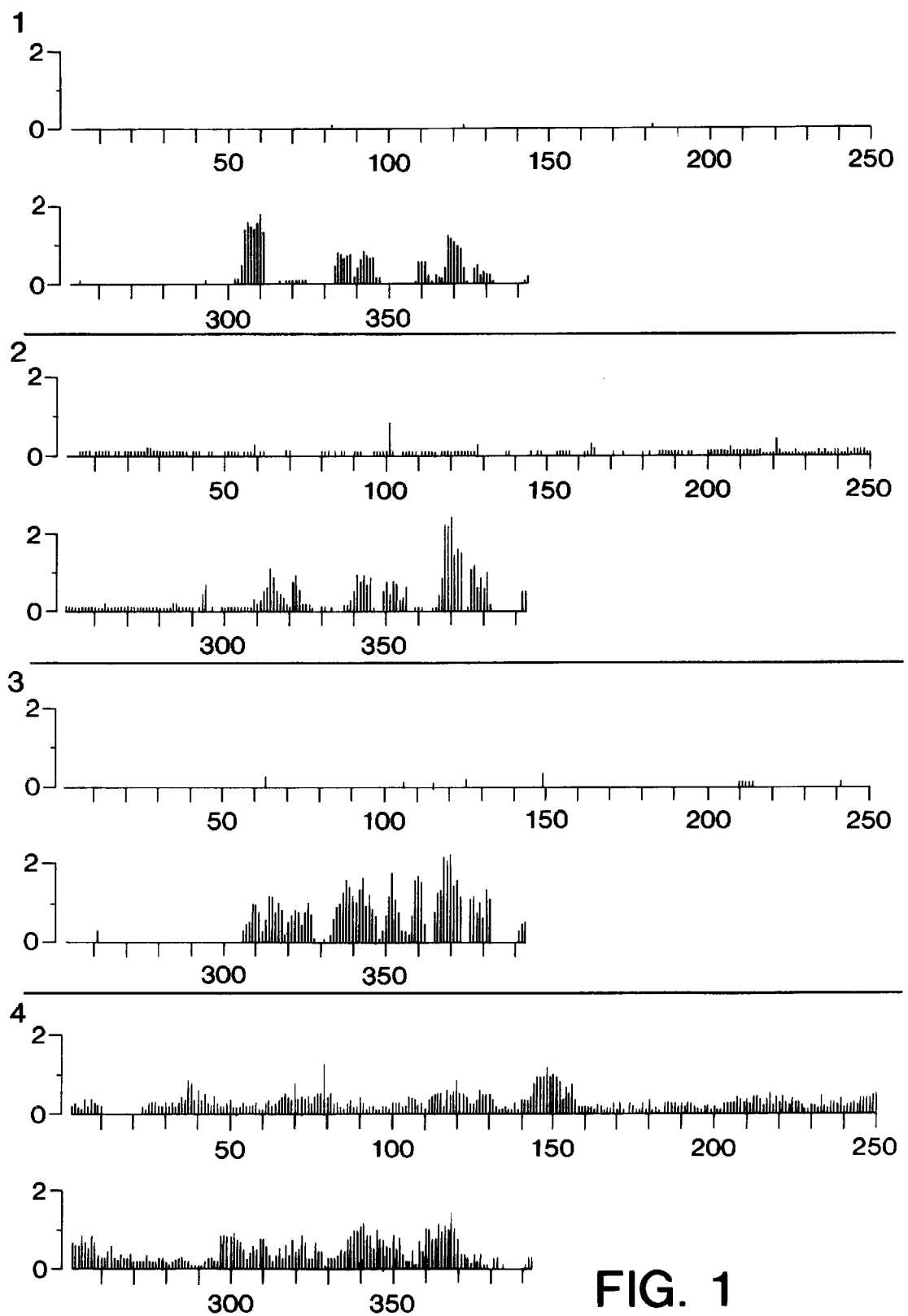
FIG. 1: Identification of the binding of IgG antibodies in the sera of 4 patients with an active EBV-infection to individual 12-mer peptides, overlapping by 11 amino acids and representing the complete AA sequence of EBV-EA(D) P47-54 (BMRF1).

The results of such a PEPSCAN analysis for four sera of individuals with an active EBV-infection are shown in FIG. 1.

From this figure it can be seen that most sera contained antibodies reactive with regions (domains) that are located in the C-terminal region of the protein, though some individuals also have antibodies to domains elsewhere in the protein.

Similar data were found with additional sets of EBV-patient sera whereas no such reactivities were found with sera from healthy controls.

Example 2

Localization of immunoreactive (peptide) domains on EBV-EA(D) P138 (BALF2)

Peptides from the entire reading frame of BALF2 were synthesised and analysed as described for Example 1.

Figure 2:
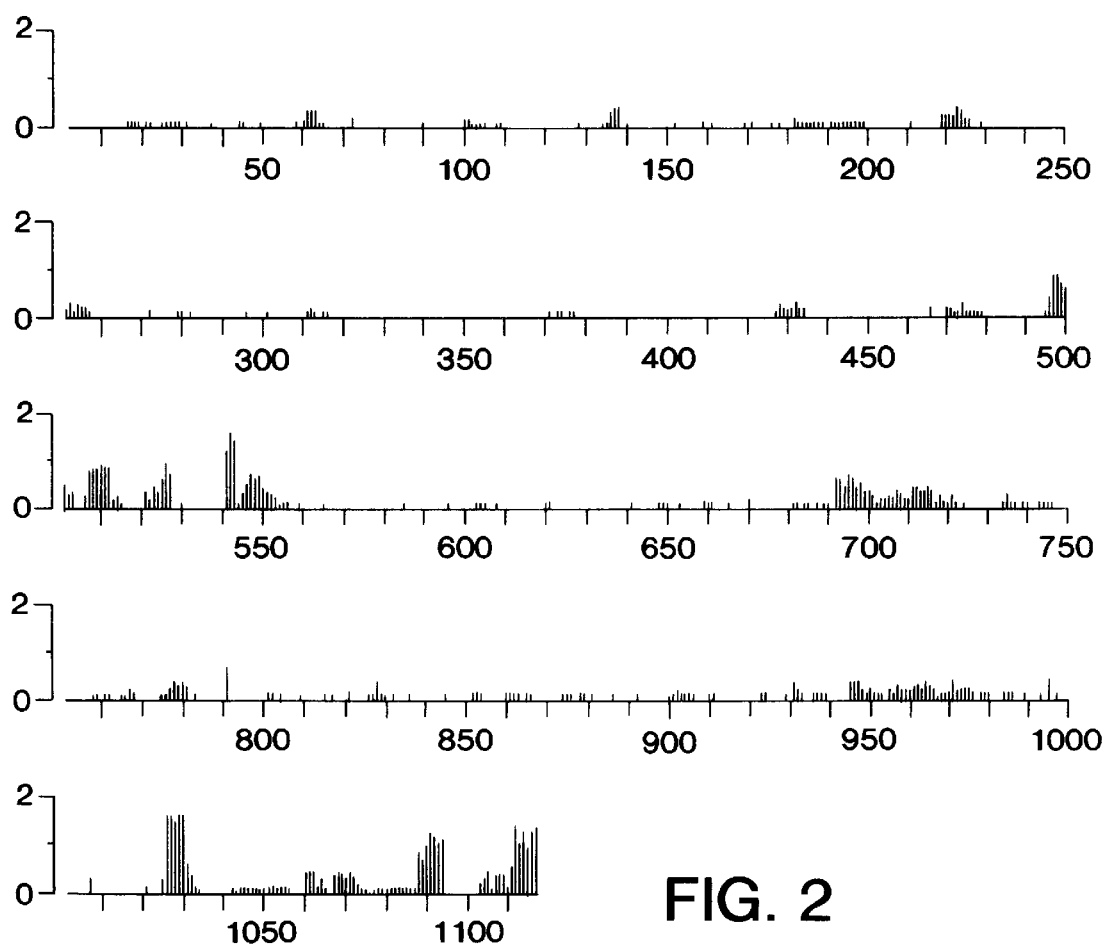
FIG. 2: Identification of the binding of IgG antibodies in the serum of a patient with an active EBV-infection to individual 12-mer peptides, overlapping by 11 amino acids and representing the complete AA sequence of EBV-EA(D) P138 (BALF2).

Results for one EBV-patient serum is shown in FIG. 2.

From this figure it can be seen that antibody reactive regions are found at multiple sites on the protein AA sequence, mostly confined to AA490-600 and to the C-terminus at AA 1000-1128.

Similar data were found with additional sera from EBV patients.

Example 3

Utilization of soluble synthetic peptides from EBV-EA(D) P47-54 for improved reactivity with human serum antibodies Selected peptides (see sequence listing) were synthesized using standard solid phase methods ((J. Amer. Chem. Soc. 85, 2149 (1963); Int. J. Peptide Protein Res. 35, 161–214 (1990)) to combine multiple PEPSCAN reactive domains into a single molecule. These peptides were coated onto the solid phase in the wells of 96-well micro-ELISA plates, usually at 1 µg/ml in coating buffer and non-bound positions were blocked with 1% bovine serum albumine in coating buffer.

In all cases peptides were coated onto the solid phase in 0.1M carbonate buffer pH 9.6.

After washing the wells with 0.1M phosphate buffered saline (pH7.4) containing 0.05% Tween-20, serum dilutions of human sera (usually 1:100) were analysed for antibody reactivity using standard procedures.

Figure 3:
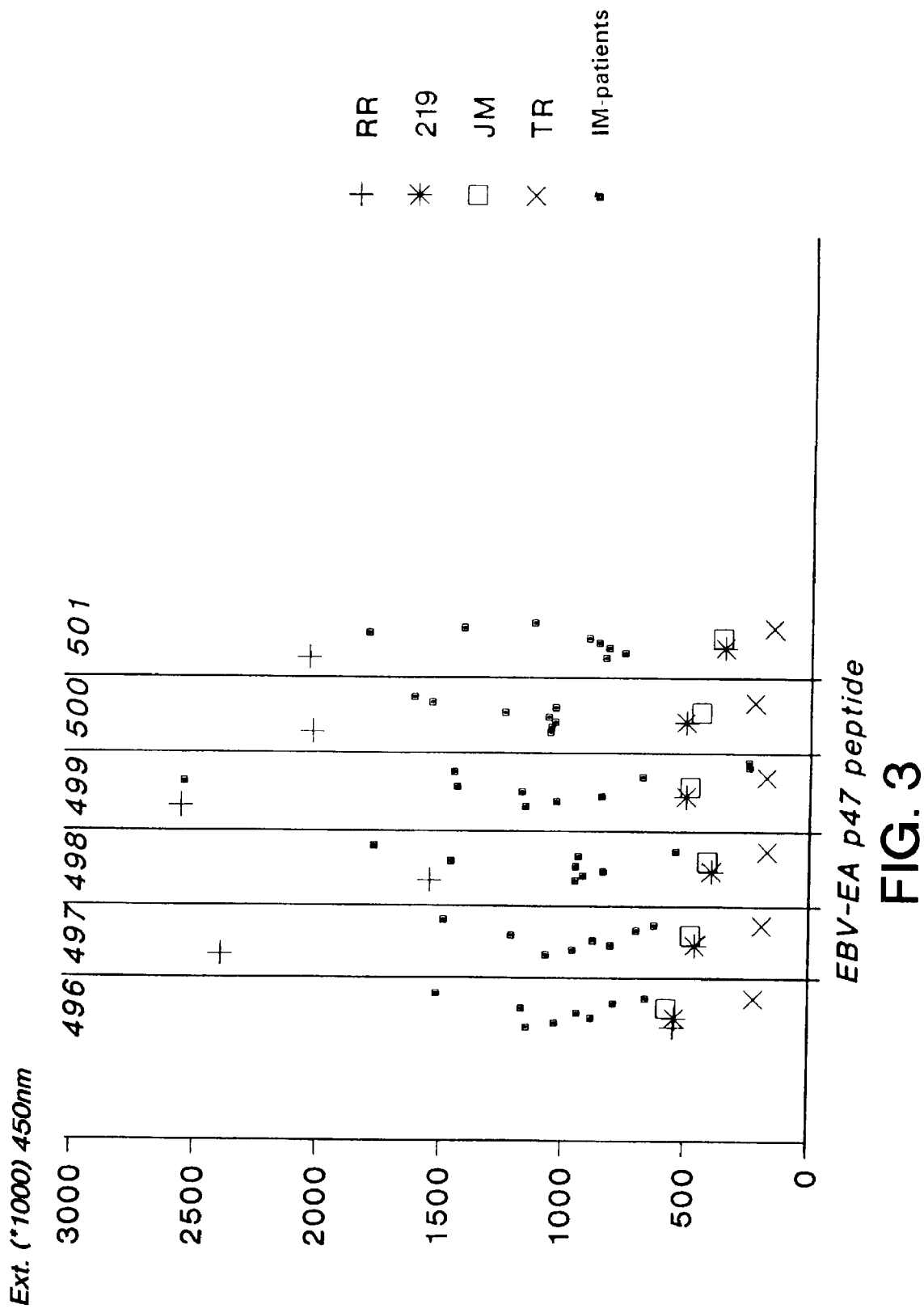
FIG. 3: Detection of (IgG) antibodies to individual synthetic peptides representing combinations of immunoreactive domains of EA(D) P47-54. Peptide sequences are described in the sequence listing.

The result of such an analysis is shown in FIG. 3.

Peptide #501, which is a combination of peptide #499 and #500, is constructed by introducing at the C-terminus of #499 a cysteine-residue, and at the N-terminus of #500 a cysteine-residue, in order to link these peptides by a disulfide-bond. Other, similar techniques of combining or linking peptides (f.i. by standard solid phase synthesis) are known in the art. If the standard solid phase technique is used, the introduction of the two cysteine-residues is not necessary, and therefore these two residues can be deleted from the amino acid sequence (SEQ.ID.No. 6; AA 20 and 21)).

From this figure it can be seen that peptides #500 and #501 show the best discrimination between positive anti-EA(D) reactions with sera from EBV-infected patients and negative reactions with sera from healthy control donors which are either latently infected with EBV (JM and 219) or negative for EBV (TR). Peptides #496 and #497 showed a similar performance as reference peptide #498 which is a N-terminal extension of a peptide of P47-54 shown by others to include an antibody reactive AA sequence (J. Clin. Lab. Anal. 1 (1987) p.140–145).

Thus especially peptides #500 and #501 represent new reagents with improved reactivity for detection of anti-EA(D) antibodies.

Example 4

Utilization of synthetic peptides from EBV-EA(D) P138 for improved reactivity with human serum antibodies Similarly as described in Example 3 selected synthetic peptides reagents were made to include immunoreactive domains of P138 (see sequence listing) and these were tested in ELISA using standard procedures.

In all cases peptides were coated onto the solid phase using carbonate buffer at pH9.6 and sera were tested at 1:100 dilution.

FIG. 4A shows the results of an experiment with peptides coated to the solid phase at pH9.6 and FIG. 4B shows that the reactivity of one of these peptides is improved by coating at pH7.2 in stead of pH9.6.

From these studies it can be seen that selected peptides from EBV-EA(D) P138 can be utilized (depending upon the coating condition) to detect anti-EA(D) antibodies specifically in sera from EBV-patients. Sera from healthy controls with a latent EBV-infection show a negative reaction similar to EBV-seronegative donors.

Example 5

Combination of selected peptides in a single assay for improved sensitivity

An additional advantage of the selected reagents is the possibility to combine peptides of different EA(D) proteins into a single assay to improve the overall sensitivity for detecting anti-EA(D) antibodies.

This is demonstrated in FIG. 5 showing the serum IgG reactivity of random mononucleosis patients to peptides #501 (P47-54; SEQ.ID.6) and G-34-R (P138; SEQ.ID.7) alone and in a 1:1 combination coated in the same well.

Furthermore, in FIGS. 6–7, the combination of selected peptides in a single assay is demonstrated (the detection of IgM, IgG and IgA anti-EA(D) in the clinical settings according to Examples 3–4 is demonstrated in FIGS. 7A–C.

It is clear from these figures that the combination of selected peptides increased the sensitivity of detecting anti-EA(D) antibodies.

Example 6

Immunoblot analysis of monoclonal antibodies EBV.OT13B, EBV.OT13D, EBV.OT13N, and EBV.OT14E Several nuclear extracts (nuclear extract of HH514 cells induced for expression of virus structural proteins (VCA), nuclear extract of HH514 cells induced for expression of EA proteins by blocking viral DNA replication with PAA (EA), nuclear extract of X50/7 cells expressing only latent phase EBV-genes (X50/7), and nuclear extract of EBV-negative Burkitt Lymphoma cell line BJAB (BJAB)) were separated by denaturing SDS-PAGE under reducing conditions and transferred to nitrocellulose sheets by standard procedures, which are known in the art.

From this immunoblot an immunoblot-analysis was performed using monoclonal antibodies EBV.OT13B (FIG. 9B), EBV.OT13D (FIG. 9D), EBV.OT13N (FIG. 8B), and EBV.OT14E (FIG. 8B) with these EBV nuclear extracts.

---

I claim:

1. An isolated peptide which is immunochemically reactive with antibodies to Epstein-Barr virus consisting of at least one amino acid sequence selected from the group consisting of SEQ ID NO:1 SEQ ID NO:2, SEQ ID NO:4, SEQ ID NO:5, SEQ ID NO:7, SEQ ID NO:8, SEQ ID NO:9, and SEQ ID NO:10.

2. An isolated peptide which is immunochemically reactive with antibodies to Epstein-Barr virus, wherein the peptide consists of at least one immunogenic determinant of an amino acid sequence selected from the group consisting of SEQ ID NO:1, SEQ ID NO:2, SEQ ID NO:5, SEQ ID NO:7, SEQ ID NO:8, SEQ ID NO:9, and SEQ ID NO:10.

3. The peptide according to claim 1, which has the amino acid sequence of SEQ ID NO:6.

4. A composition comprising one or more peptides of claim 1, having a labelling substance attached thereto and having the said labeled peptide or peptides being attached to a solid support.

5. A composition comprising one or more peptides of claim 1 being attached to a solid support.

6. A test kit comprising at least one peptide according to claim 1, wherein the said peptide is attached to a solid support.

7. The test kit of claim 6, which further comprises at least one peptide according to claim 1, which is labelled with a labelling substance.

8. The test kit of claim 6, which further comprises a labelled anti-EBV antibody.

* * * * *

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear (i i) MOLECULE TYPE: peptide (v i) ORIGINAL SOURCE:
    (A) ORGANISM: Epstein-Barr virus (x i) SEQUENCE DESCRIPTION: SEQ ID NO: 1:

```
Tyr Met Pro Pro Ala Ser Asp Arg Leu Arg Asn Glu Gln Met Ile Gly
1               5                   10                  15
Gln Val Leu Leu Met Pro Lys
                20
```

(2) INFORMATION FOR SEQ ID NO: 2:

(i) SEQUENCE CHARACTERISTICS:
        (A) LENGTH: 28 amino acids
        (B) TYPE: amino acid
        (C) STRANDEDNESS:
        (D) TOPOLOGY: linear (i i) MOLECULE TYPE: peptide (v i) ORIGINAL SOURCE:
        (A) ORGANISM: Epstein-Barr virus (x i) SEQUENCE DESCRIPTION: SEQ ID NO: 2:

```
Phe Asn His Ala Ser Glu Glu Ala Ala Ala Ser Thr Ala Ser Glu Pro
1               5                   10                  15
Glu Asp Lys Ser Pro Arg Val Gln Pro Leu Gly Thr
                20                  25
```

(2) INFORMATION FOR SEQ ID NO: 3:

(i) SEQUENCE CHARACTERISTICS:
        (A) LENGTH: 13 amino acids
        (B) TYPE: amino acid
        (C) STRANDEDNESS:
        (D) TOPOLOGY: linear (i i) MOLECULE TYPE: peptide (v i) ORIGINAL SOURCE:
        (A) ORGANISM: Epstein-Barr virus (x i) SEQUENCE DESCRIPTION: SEQ ID NO: 3:

```
Pro Ala Arg Pro Glu Thr Pro Ser Pro Ala Ile Pro Ser
1               5                   10
```

(2) INFORMATION FOR SEQ ID NO: 4:

(i) SEQUENCE CHARACTERISTICS:
        (A) LENGTH: 19 amino acids
        (B) TYPE: amino acid
        (C) STRANDEDNESS:
        (D) TOPOLOGY: linear (i i) MOLECULE TYPE: peptide (v i) ORIGINAL SOURCE:
        (A) ORGANISM: Epstein-Barr virus (x i) SEQUENCE DESCRIPTION: SEQ ID NO: 4:

```
Thr Val Ser Pro Ser Pro Ser Pro Pro Pro Pro Pro Arg Thr Pro Thr
1               5                   10                  15
Trp Glu Ser
```

(2) INFORMATION FOR SEQ ID NO: 5:

(i) SEQUENCE CHARACTERISTICS:
        (A) LENGTH: 26 amino acids (B) TYPE: amino acid
(C) STRANDEDNESS:
(D) TOPOLOGY: linear (ii) MOLECULE TYPE: peptide (vi) ORIGINAL SOURCE:
(A) ORGANISM: Epstein-Barr virus (xi) SEQUENCE DESCRIPTION: SEQ ID NO: 5:

```
His Ser Ser Asn Thr Ala Leu Glu Arg Pro Leu Ala Val Gln Leu Ala
1               5                   10                  15
Arg Lys Arg Thr Ser Ser Glu Ala Arg Gln
            20                  25
```

(2) INFORMATION FOR SEQ ID NO: 6:

(i) SEQUENCE CHARACTERISTICS:
(A) LENGTH: 47 amino acids
(B) TYPE: amino acid
(C) STRANDEDNESS:
(D) TOPOLOGY: linear (ii) MOLECULE TYPE: peptide (vi) ORIGINAL SOURCE:
(A) ORGANISM: Epstein-Barr virus (ix) FEATURE:
(A) NAME/KEY: Disulfide-bond
(B) LOCATION:21..22
(D) OTHER INFORMATION:/note= "The two cysteine residues (AA 20 and AA 21) are introduced to link two separate peptides."

(xi) SEQUENCE DESCRIPTION: SEQ ID NO: 6:

```
Thr Val Ser Pro Ser Pro Ser Pro Pro Pro Pro Pro Arg Thr Pro Thr
1               5                   10                  15
Trp Glu Ser Cys Cys His Ser Ser Asn Thr Ala Leu Glu Arg Pro Leu
            20                  25                  30
Ala Val Gln Leu Ala Arg Lys Arg Thr Ser Ser Glu Ala Arg Gln
        35                  40                  45
```

(2) INFORMATION FOR SEQ ID NO: 7:

(i) SEQUENCE CHARACTERISTICS:
(A) LENGTH: 34 amino acids
(B) TYPE: amino acid
(C) STRANDEDNESS:
(D) TOPOLOGY: linear (ii) MOLECULE TYPE: peptide (vi) ORIGINAL SOURCE:
(A) ORGANISM: Epstein-Barr virus (xi) SEQUENCE DESCRIPTION: SEQ ID NO: 7:

```
Gly Asn Phe Leu Asn Phe Ile Asp Lys Glu Asp Asp Gly Gln Arg Pro
1               5                   10                  15
Asp Asp Glu Pro Arg Tyr Thr Tyr Trp Gln Leu Asn Gln Asn Leu Leu
            20                  25                  30
Glu Arg
```

(2) INFORMATION FOR SEQ ID NO: 8:

(i) SEQUENCE CHARACTERISTICS:
(A) LENGTH: 28 amino acids
(B) TYPE: amino acid
(C) STRANDEDNESS:

-continued (D) TOPOLOGY: linear (ii) MOLECULE TYPE: peptide (vi) ORIGINAL SOURCE:
(A) ORGANISM: Epstein-Barr virus (xi) SEQUENCE DESCRIPTION: SEQ ID NO: 8:

```
Asp Ala Met Gly Glu Ala Cys Ala Ser Leu Thr Arg Asp Asp Ala Glu
1               5                   10                  15
Thr Leu Leu Ser Arg Phe Ser Val Leu Ala Asp Ser
            20                  25
```

(2) INFORMATION FOR SEQ ID NO: 9:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (vi) ORIGINAL SOURCE:
(A) ORGANISM: Epstein-Barr virus (xi) SEQUENCE DESCRIPTION: SEQ ID NO: 9:

```
Ala Gln Asp Asp Phe Ile Ser Val Ala Glu Pro Val Ser Thr Ala Ser
1               5                   10                  15
Gln Ala Ser Ala Gly Leu Leu Leu Gly Gly Gly
            20                  25
```

(2) INFORMATION FOR SEQ ID NO: 10:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (vi) ORIGINAL SOURCE:
(A) ORGANISM: Epstein-Barr virus (xi) SEQUENCE DESCRIPTION: SEQ ID NO: 10:

```
Gly Gln Gly Ser Gly Gly Arg Arg Lys Arg Arg Leu Ala Thr Val Leu
1               5                   10                  15
Pro Gly Leu Glu Val
            20
```